United States Patent [19]

Ulbers et al.

[11] Patent Number: 5,790,233
[45] Date of Patent: Aug. 4, 1998

[54] DEVICE FOR KERATOMETRIC MEASUREMENTS

[75] Inventors: Gerd Ulbers, Riggisberg; Jürg Stucki, Oberdiessbach, both of Switzerland

[73] Assignee: Haag-Streit AG, Köniz, Switzerland

[21] Appl. No.: 712,899

[22] Filed: Sep. 12, 1996

Related U.S. Application Data

[63] Continuation of PCT/IB95/01008, Nov. 15, 1995.

[30] Foreign Application Priority Data

Jan. 16, 1995 [CH] Switzerland .................. 118/95

[51] Int. Cl.$^6$ ........................................................ A61B 3/10
[52] U.S. Cl. ........................................... 351/212; 351/211
[58] Field of Search ................................. 351/212, 247, 351/246, 211, 205, 221

[56] References Cited

U.S. PATENT DOCUMENTS 2,174,308  9/1939  Hartinger .

FOREIGN PATENT DOCUMENTS

| 963094 | 7/1964 | France . |
| 2345978 | 3/1977 | France . |
| 4316782 | 5/1993 | Germany . |
| 2177813 | 1/1987 | United Kingdom . |

*Primary Examiner*—Hung X. Dang
*Attorney, Agent, or Firm*—Notaro & Michalos PC

[57] ABSTRACT

A the device for carrying out keratometric measurements has a beam splitter (9) which can be pivoted about a pivot axis (37) in a defined way. The beam splitter (9) serves for dividing and simultaneously for recombining the partial beams. The pivot axis (37) of the beam splitter (9) extends perpendicularly to the optical axis (o) of the beam (5a) reflected by the curve region (K) to be measured of the cornea of the living eye (A), as well as perpendicularly to the connection line of the test objects (B, Q). By pivoting the beam-splitter cube (9) the image height imaging (h') of the reflection points (Y,Z) can be doubled and shifted relative to one another in a defined way according to the selected pivot angle ($\alpha$). The device has a compact construction and permits simple and exact operation.

12 Claims, 2 Drawing Sheets

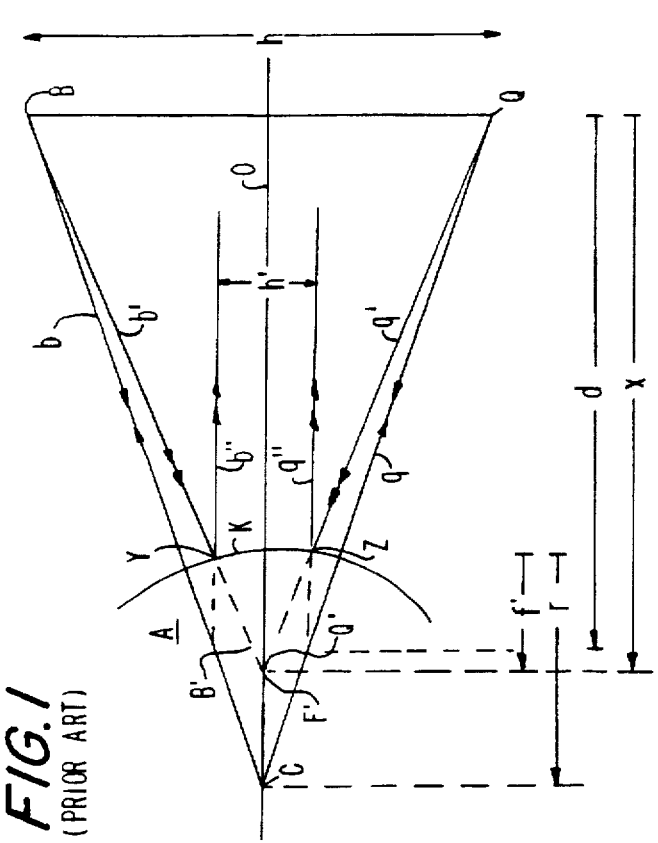
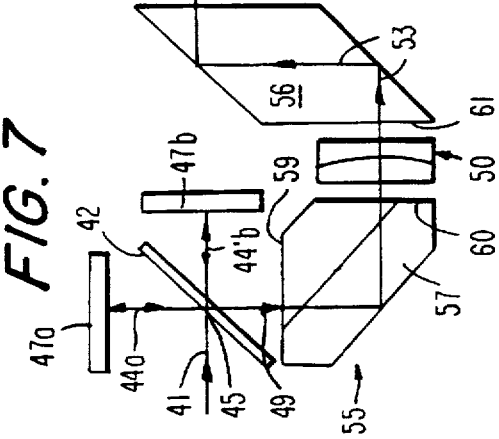
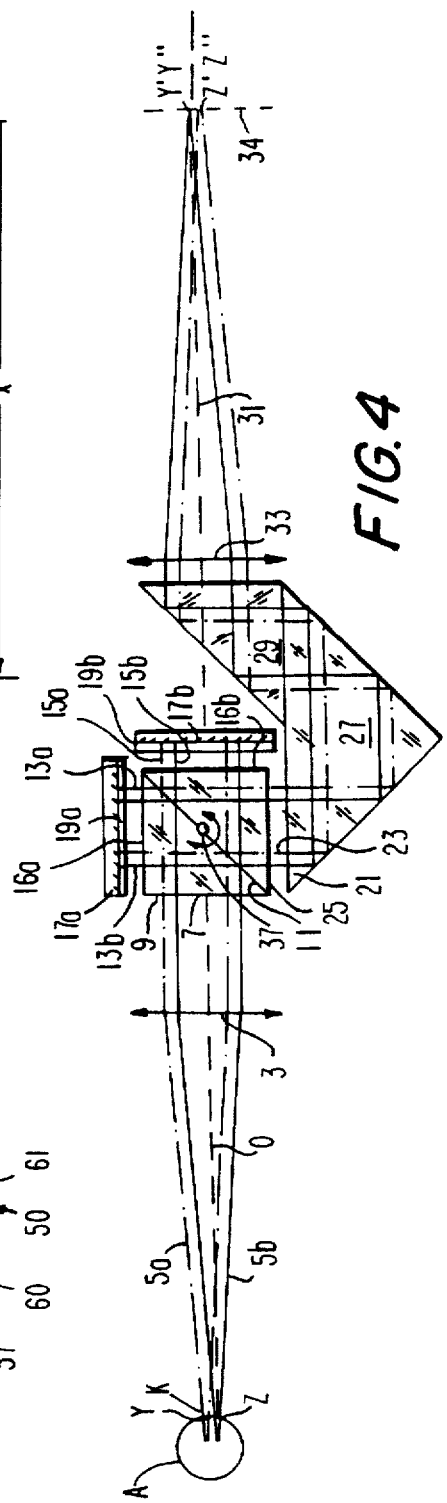
FIG. 1 (PRIOR ART)
FIG. 4
FIG. 7

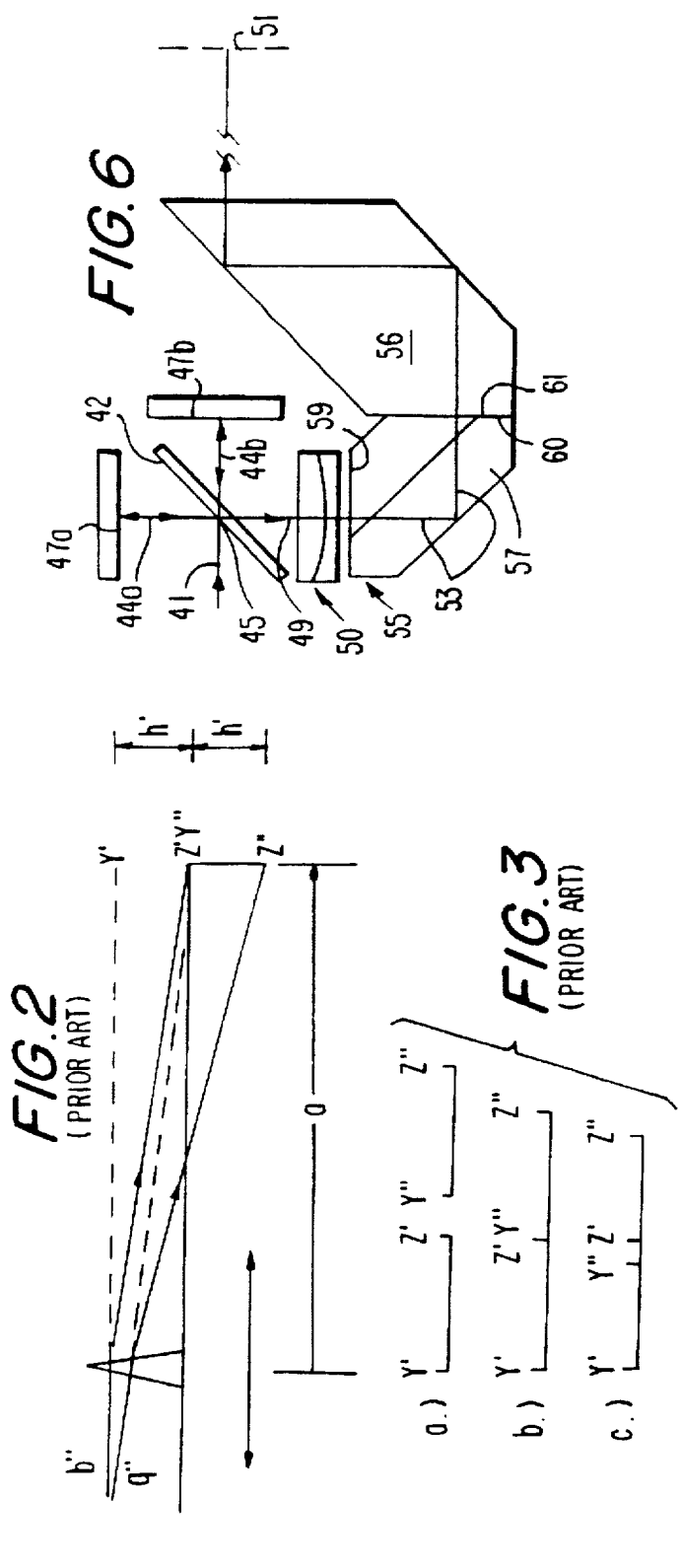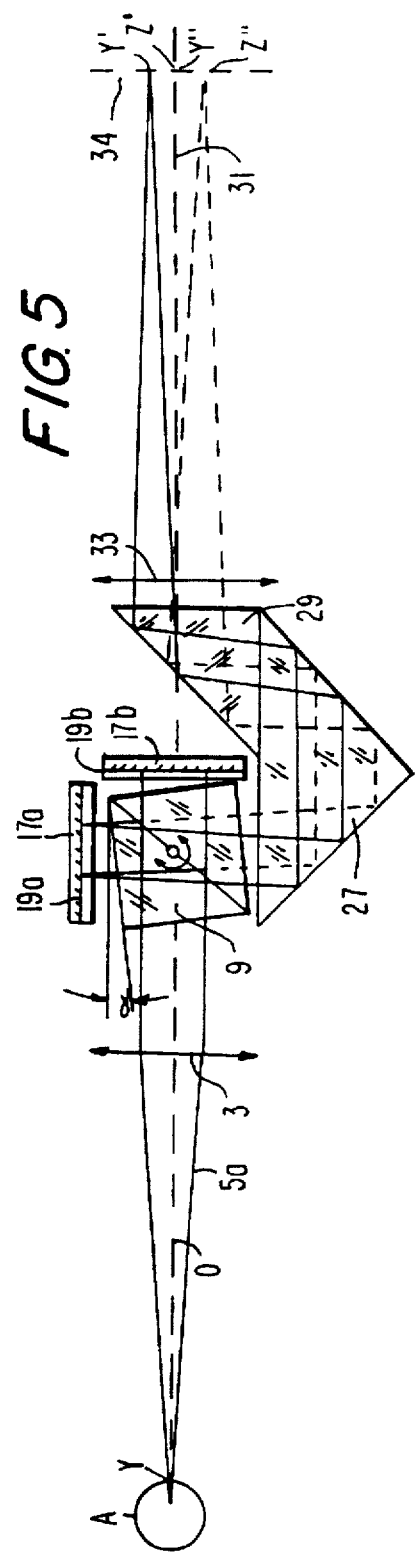

DEVICE FOR KERATOMETRIC MEASUREMENTS

CROSS-REFERENCE TO RELATED APPLICATION

This is a continuation-in-part of International Application PCT/IB95/01008, with an international filing date of Nov. 15, 1995, now abandoned.

FIELD AND BACKGROUND OF THE INVENTION

The invention relates to a device for carrying out keratometric measurements. For fitting contact lenses, for example, the radius of curvature r of a specific surface region K of the cornea must be determined on the living eye. This determination is referred to as keratometry. Herein the surface region, which here in an approximation is seen as spherical, acts as a convex mirror for the incident rays. Building on Janet Stone "Contact Lens Practice", Montague Ruben and Michel Guillon, Chapman & Hall, London, ISBN 0 412 35120 X, 1994, Chapter 16, pp. 283–311, in the following referred to as [1], according to the FIG. 1 shown there, follows:

Let B and Q be two luminous objects at interval h, the so-called object height. Rays q and b, starting from these object points B and Q in the direction of point C of a circle of the surface region K are reflected back onto themselves. Rays b' and q' in the direction of the imaginary focal point F of the spherical surface region K are reflected parallel to the optical axis o as rays b" and q" from the reflection sites Y and Z onto the surface region K. Thus a virtual image height h' of an image BQ results with the virtual image points B' and Q'. The distance from the vertex of the curve region K to the focal point F is the focal length f' which is one half of the radius r of the curve region K. Let the distance of object BQ to the focal point F be x. Angles YF'Z and BF'Z are identical. It thus follows that $$\frac{h'}{h} = \frac{f'}{x} \text{ with } r = 2f' \text{ yields } \frac{h'}{h} = \frac{r}{2 \cdot x} \quad [F\ 1]$$

If the object BQ is far enough from the surface region K, its virtual imaging B'Q' takes place in the focal plane [F'].

$$r = \frac{2x \cdot h'}{h} \text{ i.e. with the above approximation } r = \frac{2d \cdot h'}{h} \quad [F\ 2]$$

where d is the image-object distance.

The radius r of the curve region K is thus a function of the three parameters d, h and h'.

The reflecting image points Y and Z move on the cornea since the eye during the measuring cannot be completely immobilized. However, they always move together. For this reason, the two reflection points according to the prior art described in [1] are doubled with a prism arrangement according to FIG. 2. Depending on the position of the prism, instead of the points Y and Z to be observed, the points Y', Y", Z' and Z" result. The prism can now be inclined so that the intervals Y'Z' and Y"Z" are distanced from each other, overlap or are arranged adjacent to each other so that they adjoin, as depicted in FIG. 3.

To generate a variable distance of the two doubled intervals Y'Z' and Y"Z", according to [1], Bausch & Lomb pp. 288ff., Chapter 16.3.4, a rotating disk is used comprising two pairs of openings disposed radially opposing each other. A first pair of openings comprises opposing prisms while the other pair does not have any prisms. The required adjacent distance variation is achieved through a distance variation of the rotating disk. Furthermore, pivotable planar glass plates [1], Rodenstock C-BES, page 289 and reflecting prisms [1], Zeiss, page 289 are used.

From GB-B 963 094 is known a keratometer which has a stationary beam-splitting cube with rhombic cross section and two mirrors arranged at right angles to each other. With the two mirrors the beam divided by the beam-splitting cube was reflected back to it and superimposed there. The two mirrors were disposed slidably to generate a coincidence of the two marks.

From a French Patent Application FR-A 2 345 978 a further device for carrying out keratometric measurements is known. The known device has a plane parallel plate pivotable about a pivot axis for generating a variable ray offset. The pivot axis of the plate was perpendicular to the optical axis of the rays of two reflection sites of the two test objects, reflected from a curve region of the cornea to be measured.

From GB-A 2 177 813 a further keratometer is known. The known keratometer operates with a red and green mark of which images were to be formed on the surface of the eye. It had two plane parallel plates adjustable by a settable angle which could be read. The plates served for beam offset of rays emitted by the two marks reflected on the surface of the eye. The red beam was offset with the one plate and the green one with the other.

A further keratometer is described in DE-C 43 16 782. The keratometer disclosed herein comprises a stationary polarizing beam-splitting cube with several deflection prisms as well as a further beam-splitting cube for superimposing the two split beams. In each of the beam paths of the two split beams a lens was disposed. Both lenses were seated on a carrier with which the lenses could be slid in a defined way parallel to their main plane. Through the sliding of the lenses the optical axes of the partial beam paths were tilted relative to one another and the observed partial images shifted relative to one another.

Instead of the two lenses, in DE-C 43 16 782 also a pivoting mirror was used.

Common to all of these optical structures is an expensive and complex construction as well as a lack of compactness.

SUMMARY OF THE INVENTION

It is the task of the invention to create a compact as well as easily operatable arrangement for keratometric measurements.

The task is solved by using a physical beam splitter which can be pivoted in a defined way, with settable pivot angle, with which the image of the two reflection points of the two test objects (Mires) on the eye is doubled and are depicted analogous to FIGS. 2 and 3 relating to embodiments in an image plane as segments disposed one above the other.

According to H. Haferkorn, "Optik, physikalisch-technische Grundlagen und Anwendungen" VEB Deutscher Verlag der Wissenschaften, Berlin 1980, page 480, one differentiates in optics a physical and a geometric splitting of a beam of rays. As is the case in the invention, the physical beam splitting is carried out with partially transmitting surfaces. In physical beam splitting the beam cross section, and thus the light transmittance in both partial beams remains as great as in the incident beam. The light stream is divided leading to a change of the luminance in the partial beams.

In geometric beaming a portion of the beam is split off with a mirror or a prism (total reflection). In geometric beam splitting the luminance in the partial beams remains constant but the transmittance is changed.

By using reflectors cooperating with the physical beam splitter, in particular in a "Michelson" arrangement, a compact construction of the device can be achieved which is still improved by the beam guidance described below in which the incident beams of rays are preferably aligned with the emergent ones. Interference effects do not occur through the so-called "Michelson" arrangement since the coherence length of the rays used is much too small.

As beam splitter a semireflecting mirror or also the beam-splitter cube described as an example below can be used. The capacity for semireflection can be generated through a corresponding coating which reflects approximately 50% of the rays and transmits the other 50%. It is also possible to use a polarizing beam splitter. If, in addition to the polarizing beam splitter, elements (for example phase plates) rotating the plane of polarization correspondingly are placed in front of the reflectors it is possible to work with significantly lower light levels for the eye illumination. As elements rotating the plane of polarization are preferably used so-called quarter-wave plates.

To generate a variable distance of the two doubled intervals Y'Z' and Y"Z" relative to one another, it is here also possible to work with a variable image distance a. However, work is preferably carried out with a fixedly set distance in order to avoid having to carry out readjustments of the imaging conditions.

For optimum adjustment of the keratometer and for determining the surface radii in several direction, it must be adjusted to the eye and also be rotated about its horizontal optical axis. So that with this rotation of the keratometer simple adjustability is possible, after the beam splitter/combiner an image-rotation element is inserted into the beam path. Hereby the image rotation subsequently takes place analogously to the rotation of the keratometer and no longer with the twofold angle of rotation as is the case in the above specified keratometer disclosed in GB-B 963 094.

BRIEF DESCRIPTION OF THE DRAWINGS

In the following, examples of the device according to the invention will be explained in further detail in conjunction with the drawings. Further advantages of the invention are evident in the following description. In the drawings:

FIG. 1 is a diagram showing the principle of keratometry according to [1], page 288, with the caption characterized with FIG. 16.9 in this publication being exchanged with that of FIG. 16.8, FIG. 2 is a drawing showing the doubling principle using a prism according to [1] FIG. 16.8, page 287, wherein here also the exchange of the captions should be noted, FIG. 3 is a representation of the doubling principle of the image heights with separate, adjacent and overlapping image heights representation, FIG. 4 shows the sketched beam path in the device according to the invention with null setting of the beam splitter wherein here in the representation of the beams of rays reflected from the cornea their edge rays and in FIG. 1 their central rays are drawn.

FIG. 5 is a view like FIG. 4 but with pivoted beam splitter, wherein here to avoid an overloading of the representation of the beam path, only a single image point or reflection point is depicted, FIG. 6 a variant of the keratometer shown in FIGS. 4 and 5, and FIG. 7 shows a variant of the keratometer shown in FIG. 6, in which the focusing lens is disposed at another location in the beam path.

DESCRIPTION OF THE PREFERRED EMBODIMENT

The device 1 depicted in FIGS. 4 and 5 has a collimator 3 which collimates the beams of rays 5a and 5b reflected from the reflection points Y and Z. The reflection points Y and Z are located on the surface region K of the cornea of a living eye A whose radius of curvature r is to be determined with the device according to the invention. As described above, the reflection points Y and Z are starting from the object points (Mires) B and Q illuminated with a mutual distance h. The illumination optics used for this purpose will here not be described further.

The collimated beams of rays emerging from the reflection points Y and Z impinge on the coated incident face 7 of a beam-splitter cube 9. The beam-splitter cube 9 is a physical polarizing beam splitter whose face of division 11 is inclined at a 45 degree angle relative to the incident face 7, wherein for example the partial beams 13a and 13b of the incident beams 5a and 5b reflected at the face of division 11 have a plane of polarization parallel to the plane of drawing of FIG. 4 and the transmitted partial beams 15a and 15b a plane of polarization perpendicular to it.

Perpendicular to the emergent faces 16a and 16b, also coated, of partial beams 13a, 13b, 15a and 15b each a reflector 17a and 17b is disposed. In front of each reflector 17a is disposed a phase plate 19a, or respectively 19b, for rotating the plane of polarization of the rays penetrating them. Each plane of polarization of the partial beams 13a and 13b, or respectively 15a and 15b, emerging from the coated emergent faces 16a and 16b, is now rotated by the phase plate 19a, respectively 19b, by 45 degrees, is rotated at reflector 17a, respectively 17b, by 180 degrees and a further phase rotation by 45 degrees when it passes again through the particular phase plate 19a or 19b. The plane of polarization of the partial beams 13a and 13b as well as 15a and 15b, consequently, has been rotated by 270 degrees (identical to 90 degrees). Thus, the partial beams 13a and 13b reflected by reflector 17a penetrate the face of division 11, while the partial beams 15a and 15b, reflected by reflector 17b, are reflected by the face of division 11. The partial beams 13a and 15a as well as 13b and 15b leave the beam-splitter cube 9 as beams 21 and 23 through its coated emergent face 25. The beams 21 and 23 are deflected by an arrangement of two prisms 27 and 29 after three total reflections such that the optical axis o of the beams of rays 5a and 5b incident onto the beam-splitter cube 9 are approximately aligned with the optical axis 31 of the beams 21 and 23 exiting the prism arrangement 27/29. These emergent collimated beams 21 and 23 are focused with a focusing lens 33 on an image plane 34. In the image plane 34 the images Y', Y", Z', Z" of the reflection sites Y and Z overlap on the eye A if the beam-splitter cube 9 is disposed in the center position shown in FIG. 4.

To determine the radius r of the corneal region K to be measured, now according to the explanations in connection with FIGS. 2 and 3 the images Y', Y", Z' and Z" are doubled and imaged superimposed. To pull apart the images Y', Y", Z' and Z" which in the center position of the beam-splitter cube 9 overlap, this [the cube] is pivoted about its pivot axis 37, perpendicular to the optical axis o and perpendicular to the connection line of the object points B and Q, about the angle α according to the representation in FIG. 5. To avoid overloading FIG. 5, only the beam path of the one beam of rays 5a is shown, emergent from the one Y of the two reflection points Y and Z on the eye A.

Pivoting the beam-splitter cube 9 by the angle α yields analogously to the explanation in connection with FIG. 2 an adjustable enlargement ratio P dependent on angle α. The optical distance of the image plane 34 from the beam-splitter cube 9, taking into consideration an optical path extension through the two prisms 27 and 29, corresponds to the above distance a.

To determine the image height, it is only necessary that in the invention the beam-splitter cube 9 is pivotable and its adjusted pivot position determinable.

As explained above, the phase plates 19a and 19b can be omitted if with the two objects B and Q a sufficient light intensity is applied to the eye A. In this case, a polarizing beam splitter is also no longer used. It is also no longer necessary, as shown in FIGS. 4 and 5, that the beam is guided via the two prisms 27 and 29. It is only necessary that the partial beams 13a, 13b, 15a and 15b are combined in the image plane 34 in the manner shown. However, the beam must in this case and guided differently. The embodiment variant shown in FIGS. 4 and 5 is distinguished by its compactness and operational reliability as well as low illumination strength required for the eye A.

Of disadvantage in said embodiment variants, as depicted in FIGS. 4 and 5, is that with a rotation of the keratometer about its axis, which is essentially identical with the optical axis 31, the images projected onto the eye A from B and Q rotate with the twofold rotational speed of the keratometer. I.e. the apparent rotational angle is twice as great as the actual.

As shown in FIGS. 6 and 7, this problem is solved thereby that in the beam path of the beams combined by beam splitters an image-rotation element is inserted. As an image-rotation element is here used a ridge prism situated below 45 degrees with a ridge angle of 90 degrees. It is understood that other image-rotating elements, such as for example corresponding mirror configurations, can also be used.

A configuration example of optical elements according to the above requirements is shown in FIG. 6. The beam of rays, analogous to the beams of rays 5a and 5b, collimated by a collimator lens (analogous to 3 in FIGS. 4 and 5) not shown, is denoted by the reference number 41. Instead of the beam-splitter cube 9 a coated plate 42 is used in the component configuration of FIG. 6. The plate 42 splits the incident beam 41 approximately equally into two beams 44a and 44b. It can be pivoted about an axis 45 which extends analogously to axis 37. Two mirrors 47a and 47b are disposed parallel to axis 45 at an angle of 90 degrees with respect to each other. In the resting position the plate 42 is disposed at 45 degrees to the two mirrors 47a and 47b. The two mirrors 47a and 47b, analogously to mirrors 17a and 17b, reflect the incident rays 44a and 44b back to plate 42 for superposition. After combination, the rays 49 are focused analogously to the focusing lens 33 with a focusing lens 50 on an image plane 51 analogous to image plane 34. In the focusing cone 53, the beam traverses a ridge prism 55 and a deflection prism 56. The two ridge faces, with only one being shown in FIGS. 6 and 7 having the reference number 57, are disposed at 90 degrees. The ridge is disposed at 45 degrees to the incident beam 41 and perpendicularly to the pivot axis 45. The image is rotated with the ridge prism 55 from the incident to the emergent beam 53. The beam incident face 59 of the ridge prism 55 is parallel to axis 45 and perpendicular to beam 53 in its center position. The emergent face 60 of the ridge prism 55 is in contact with the incident face 61 of the reverse prism 56 so tightly that no reflection takes place. The emergent face of the deflection prism 56 is also perpendicular to the emergent beam in its normal position (with the plate 42 at 45 degrees). In the deflection prism 56 the beam 53 is reflected twice.

Through reflection of the partial beams 44a and 44b by the two mirrors 47a and 47b and the subsequent superposition by plate 42, a space-saving optical construction is possible. This also permits to divide in half the pivot angle region of the beam splitter.

As shown in FIGS. 4 and 5, the focusing lens can now be arranged as the last part of the optical configuration. To reduce the space requirement for the optical configuration, the focusing lens, as shown in FIG. 6, can be disposed directly following the beam splitter/combiner. However, as shown in FIG. 7, the focusing lens can be disposed between the image reversal element and the deflection prism. Which configuration is chosen depends on the space requirement and the requisite focal length of the focusing lens.

The ridge prism used in FIGS. 6 and 7 as image-rotation element can also be used in the optical configurations of FIGS. 4 and 5. Other image-rotation elements (Dove, Schmidt-Pechan, . . . ) can also be used here, such as have been described for example in G. Schroeder, "Technische Optik", ISBN 3-8023-0067-X, 1974, Vogel-Verlag, Würzburg, pages 37 to 41.

We claim:

1. A keratometric measuring apparatus, comprising:
 a light source for emitting to an eye to be examined;
 a beam splitter pivotable about a pivot axis and disposed perpendicularly to an optical axis of a light beam reflected by a curve region being measured on a cornea of a pair of reflection sites of a pair of test objects, and perpendicularly to a line connecting the test objects, the beam splitter dividing the light beam into a pair of partial beams of rays and then combining the pair of partial beams of rays by partial reflection, the beam splitter being pivoted to double and shift an image height imaging of the pair of reflection sites relative to each other in a defined manner, dependent upon a selected pivot angle; and
 measuring means for measuring the eye of a patient using the beam splitter.

2. A keratometric measuring device according to claim 1, further comprising at least one reflector which reflects at least one of the two partial beams of rays back to the beam splitter.

3. A keratometric measuring device according to claim 2, wherein the pivot axis extends parallel to at least one suface of the at least one reflector.

4. A keratometric measuring device according to claim 3, further comprising an image rotation element formed as a ridge prism, the ridge prism making an angle of 45 degrees with the light beam and having a ridge angle of 90 degrees disposed in an optical beam path of the light beam following the beam splitter in which the partial beams of rays superimposable by the beam splitter extend.

5. A keratometric measuring device according to claim 2, further comprising an image rotation element formed as a ridge prism, the ridge prism making an angle of 45 degrees with the light beam and having a ridge angle of 90 degrees disposed in an optical beam path of the light beam following the beam splitter in which the partial beams of rays superimposable by the beam splitter extend.

6. A keratometric measuring device according to claim 1, further comprising a reflector for each of the partial beams of rays divided by the beam splitter, which partial beams of rays preferably form a right angle, wherein the partial beams of rays can be reflected onto themselves back to the beam splitter, in particular in a center position of the beam splitter, and extend in such a way that in the center position both partial beams of rays are superimposed at a site of an image plane of the reflection sites.

7. A keratometric measuring device according to claim 6, wherein the pivot axis extends parallel to at least one surface of the reflector.

8. A keratometric measuring device according to claim 7, further comprising an image rotation element formed as a ridge prism, the ridge prism making an angle of 45 degrees with the light beam and having a ridge angle of 90 degrees disposed in an optical beam path of the light beam following the beam splitter in which the partial beams of rays superimposable by the beam splitter extend.

9. A keratometric measuring device according to claim 6, further comprising an image rotation element formed as a ridge prism, the ridge prism making an angle of 45 degrees with the light beam and having a ridge angle of 90 degrees disposed in an optical beam path of the light beam following the beam splitter in which the partial beams of rays superimposable by the beam splitter extend.

10. A keratometric measuring device according to claim 1, wherein the beam splitter is a polarizing beam splitter.

11. A keratometric measuring device according to claim 10, further comprising a pair of phase plates, one phase plate disposed in front of one of a pair of reflectors, the other phase plate disposed in front of the other of the pair of reflectors for rotating a plane of polarization of the partial beams of rays emitted from the beam splitter by one of 90 degrees and 270 degrees, and reflecting the partial beams of rays back into the beam splitter.

12. A keratometric measuring device according to claim 1, further comprising a beam guide connected with the beam splitter, the beam guide positioned such that partial beams of rays emitted from the beam guide are approximately aligned with the light beam incident into the beam splitter.

* * * * *